(12) United States Patent
Schühly et al.

(10) Patent No.: US 9,993,492 B2
(45) Date of Patent: Jun. 12, 2018

(54) LYSOPHOSPHOLIPIDS AND LYSOPHOSPHOLIPID ANALOGUES AGAINST HONEYBEE BROOD DISEASES

(71) Applicant: University of Graz, Graz (AT)

(72) Inventors: Wolfgang Schühly, Graz (AT); Ulrike Riessberger-Gallé, Graz (AT); Javier Hernández-López, Graz (AT); Karl Crailsheim, Graz (AT)

(73) Assignee: University of Graz, Graz (AT)

( * ) Notice: Subject to any disclaimer, the term of this patent is extended or adjusted under 35 U.S.C. 154(b) by 215 days.

(21) Appl. No.: 14/892,914

(22) PCT Filed: May 22, 2014

(86) PCT No.: PCT/EP2014/060553
§ 371 (c)(1),
(2) Date: Nov. 20, 2015

(87) PCT Pub. No.: WO2014/187906
PCT Pub. Date: Nov. 27, 2014

(65) Prior Publication Data
US 2016/0106768 A1   Apr. 21, 2016

(30) Foreign Application Priority Data

May 22, 2013 (EP) .................................... 13168757

(51) Int. Cl.
*A61K 31/685* (2006.01)
*A61K 31/683* (2006.01)
*A61K 35/644* (2015.01)
*A01K 51/00* (2006.01)
*A23K 20/158* (2016.01)
*A23K 50/90* (2016.01)

(52) U.S. Cl.
CPC ............ *A61K 31/685* (2013.01); *A01K 51/00* (2013.01); *A23K 20/158* (2016.05); *A23K 50/90* (2016.05); *A61K 31/683* (2013.01); *A61K 35/644* (2013.01)

(58) Field of Classification Search
CPC .... A61K 31/685; A61K 31/683; A61K 51/00; A61K 35/644
See application file for complete search history.

(56) References Cited

U.S. PATENT DOCUMENTS

2007/0167408 A1* 7/2007 Perrissoud ........... A61K 31/675
514/80

* cited by examiner

*Primary Examiner* — Yong Chu
(74) *Attorney, Agent, or Firm* — Eversheds Sutherland (US) LLP

(57) ABSTRACT

The present invention refers to a compound selected from the group consisting of a lysophospholipid and a lysophospholipid analog for use in the treatment or prophylaxis of honeybee brood diseases, in particular American foulbrood and European foulbrood. The invention also refers to a diet composition, a sprayable composition, a dipping solution for brood combs, a beeswax composition and liposomal and microsphere- or nanosphere-based compositions, comprising a compound according to the invention, for use in the treatment or prophylaxis of bee brood diseases.

16 Claims, 2 Drawing Sheets

LYSOPHOSPHOLIPIDS AND LYSOPHOSPHOLIPID ANALOGUES AGAINST HONEYBEE BROOD DISEASES

The present invention relates to the application of lysophospholipids and analogues thereof in honeybee brood diseases.

Insect pathogen defense mechanisms are commonly attributed to i) the presence of small molecule non-specific acting molecules such as lactic acid, ii) the action of antimicrobial peptides, e.g., apidaecins in honeybees or iii) to specifically induced immune responses that infer an immunological memory. Furthermore, the interaction between gut bacteria and pathogens, e.g. the presence of an intestinal probiotic lactic acid bacteria (LAB) flora and its production of bacteriocins as part of a defense mechanism against pathogenic bacteria, has been discussed for *Apis mellifera* [Carina Audisio et al. 2011. Microbiol Res 166:1-13] and *Apis cerana japonica* [Yoshiyama & Kimura. 2009. J Invertebr Pathol 102:91-96]. Besides these, social immunity, i.e. defenses whose efficiency increases with sociability of the respective eusocial insect, play a major role, in particular for the honeybee. So far, mechanisms of resistance that are neither related to the presence of proteins or peptides nor are the result of social behavior are scarce.

American foulbrood (AFB) is a devastating bee pest that is caused by the gram-positive sporulating bacterium *Paenibacillus larvae* (*Pl*) (formerly described as *Bacillus larvae*), which occurs in several genotypes such as ERIC I and ERIC II [Genersch et al. 2006. Intern J Syst Evol Microbiol 56:501-511]. The spores of *Pl* germinate in the larvae's midgut, from where—after proliferation—they invade into the haemocoel [Yue et al. 2008. Environm Microbiol 10:1612-1620]. Infected larvae die from septicaemia and turn into soft masses. The sporulation of *Pl* occurs in the dead remains of the larva when nutrients become scarce. As a consequence of a worker bee's hygienic behaviour, the residues of the larva are removed and spores are transferred to young larvae through nursing, which starts a cycle of reinfection that may end fatal for the bee colony. Tarr [Tarr. 1937. Ann Appl Biol 24:377-384] demonstrated that vegetative stages of *Pl* are not infectious, however, the spores can remain infectious for long periods being the only infectious form of *Pl*. Due to its worldwide presence and its high infectiousness, American foulbrood poses a threat to honey production and pollination.

European foulbrood (EFB) is a bee brood disease that is caused by the gram-positive bacterium *Melissococcus plutonius* (*M. pl.*). This potentially lethal disease has an almost worldwide distribution, which outbreaks that are seasonally and often endemic. [Forsgren, 2010. J of Invertebr Pathol 103:S5-S9]. EFB leads to bee brood losses within a colony due to the killing of the larvae at an age of 4-5 days. The contagion of the larvae with *M. pl.* takes place through the ingestion of *M. pl.*-containing food. The bacterium multiplies in the honeybee's midgut and is excreted in the faeces during pupation. It can remain viable for long time and is resistant against desciccation. [Bailey 1959. J Insect Pathol 1:80-85]. The disease is transmitted by adult worker bees that come in contact with the bacterium in the bee hive. *M. pl.* grows under microaerophilic to anaerobic conditions and can be cultivated under an enriched carbon dioxide atmosphere. *M. pl.* is a close relative of the bacterium *Enterococcus*. An infection with *M. pl.* is often associated with other bacterial infections of the midgut of honeybees. Honeybee larvae are most susceptible to this bacterium at early larval stages but remain susceptible at any stage.

Honeybee larval diet is usually protected from spoiling and is kept non-contagious by components which show strong antibacterial activity, e.g., through the presence of the potent antibacterial protein defensin 1 [Ilyasov et al. 2012. J Apicultural Sci 56:115-124].

Riessberger-Gallê et al. [Riessberger-Gallê et al. 2001. J Invertebr Pathol 77:231-236] reported on a non-induced, heat-stable substance in the midgut of adult bees that shows strong activity against the vegetative stage of *Paenibacillus larvae*. It could be demonstrated that about one tenth of a preparation of homogenized midgut was capable of inhibiting the growth of *Pl* in a test tube using a volume of 1.0 ml. The antimicrobial activity of adult honeybee midgut was not significantly reduced after heat treatment, ethanolic precipitation and the application of proteases. Moreover, it was found that homogenized larvae from day 3 on showed increasing activity against *Pl* [Crailsheim & Riessberger-Gallê. 2001. Apidologie 32:91-103; Wedenig et al. 2003. Apidologie 34:43-51].

WO 2007/027636 A2 describes treatment of conditions such as sepsis, septic shock, systemic inflammatory response syndromes and SIRS, caused by gram-positive bacteria by administration of compositions containing a phospholipid, a neutral lipid and a bile acid or a bile acid salt.

WO 9926632 A1 discloses that phospholipids such as MPPA and DPPS show an antimicrobial effect against gram-negative and gram-positive bacteria, wherein the phospholipids may be combined with antibiotics, antimicrobials, antifungal, antiviral and antiprotozoal drugs for treatment of infectious diseases.

It is well known in the art that free mono- and poly-unsaturated fatty acids possess antibiotic activity which was also shown against *Paenibacillus larvae* [Feldlaufer et al. 1993. Adipologie 24:95-99]. However, these free fatty acids exhibit a high toxicity with respect to honeybee larvae and, thus, are not suitable for treatment or prophylaxis of AFB.

Lysophosphatidylcholine was reported to have antimicrobial activity against gram-positive *Bacillus subtilis* through an autolytic mechanism. The antimicrobial activity depends on the carbon-chain length of the acyl moiety in the LPC molecule, being most effective with palmitoyl LPC [Tsuchido. 1994. Appl Microbiol Biotechnol 41:106-109].

Methods for making lysophosphatidylcholine are disclosed in EP 0882136 A1.

No globally applicable treatment of bee brood diseases, in particular American foulbrood and European foulbrood, are available to date.

While antibiotics are frequently used in the United States of America, Canada and China for treatment of *Pl* and *M. pl.* infections [Gochnauer 1951. Minn Home Fam Sci 9:15; Oldroyd et al. 1989. Austr J Agric Res. 40:691-697], the use of antibiotics is forbidden in Europe as this inevitably leads to formation of resistance [Miyagi et al. 2000. J Invertebr Pathol 75:95-96] and to detectable residues in bee products. In most European states AFB and EFB are notifiable bee pests and bee colonies infected with *Pl* or *M. pl.* have to be burnt, leading to considerable economic losses for apiculturists. Consequently, there is a great demand for a safe treatment option against American foulbrood and European foulbrood, respectively, which is substantially free from side effects.

It is an object of the present invention to provide a new and safe option for treatment and prevention of bee honeybrood diseases.

In particular, it is an object of the present invention to provide a new and safe option for treatment and prevention of bee brood diseases caused by gram-positive bacteria, in particular for treatment and prevention of American foulbrood caused by the gram-positive *Paenibacillus larvae* and European foulbrood caused by *Melissococcus plutonius*, without utilization of antibiotics.

The present invention refers to a compound selected from the group consisting of a lysophospholipid and a lysophospholipid analogue for use in the treatment or prophylaxis of bee brood diseases.

Figure 1:
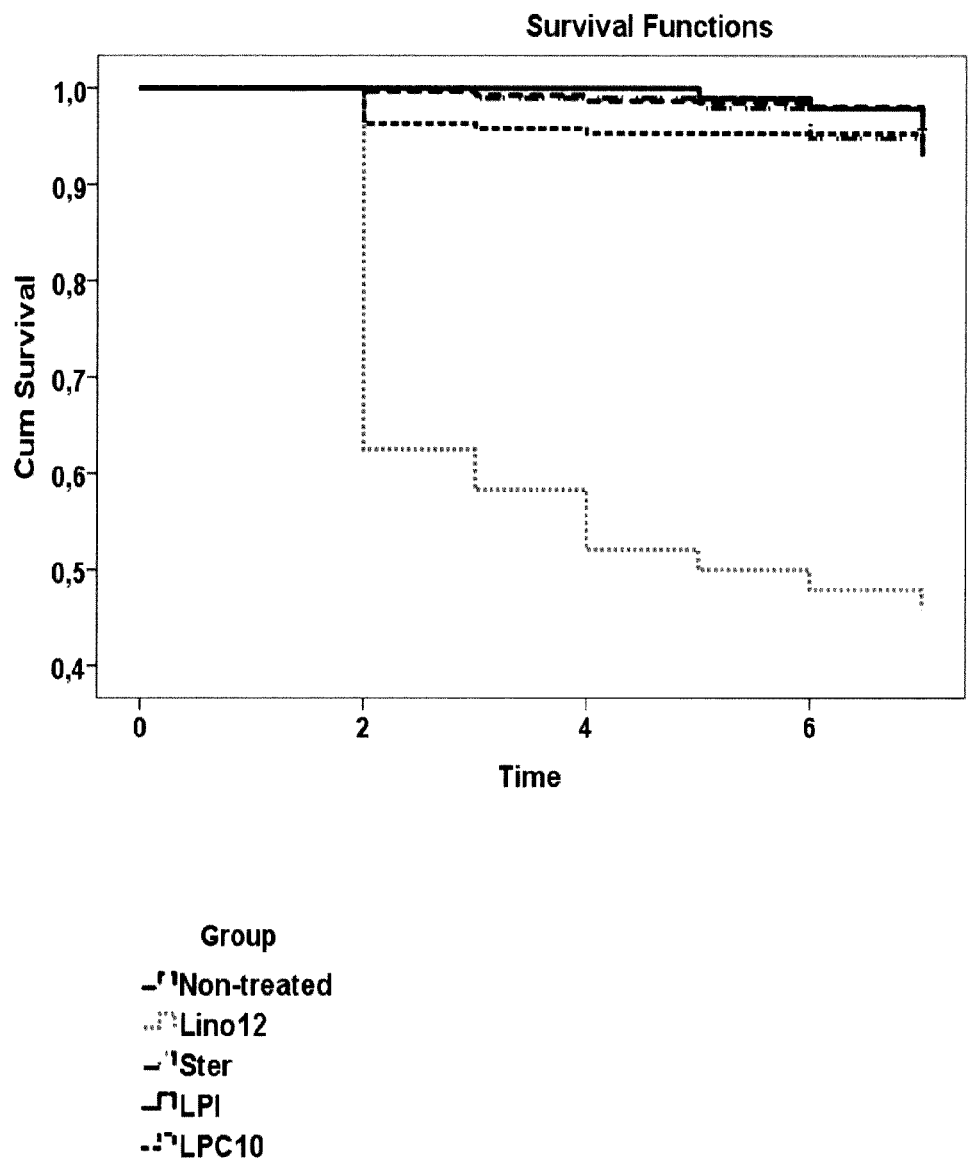
FIG. 1 depicts the survival rates of larvae fed with different substances.

Based on the observation that the midgut homogenate from adult honeybees (*Apis mellifera*) shows a strong antibacterial activity against the causative agent of American foulbrood (AFB), *Paenibacillus larvae* (*Pl*), and European foulbrood (EFB), *Melissococcus plutonius* (*M. pl.*) a bioactivity-guided isolation and characterization of the active principle in honeybee midgut was carried out. Experiments with the active fraction obtained from semi-preparative HPLC fractionation indicated that the substance did not belong to the known antibacterial proteins or peptides. A subsequent high resolution mass spectrometric analysis then revealed the presence of the 1-O-oleoyl-sn-glycero-3-phosphocholine as compound responsible for antibacterial activity against *Pl* and *M. pl.*. Antibacterial concentrations of lysophosphatidylcholine could also be detected in larvae. The presence of lysophosphatidylcholine could also be demonstrated in the midguts of wasps and bumblebees, whose homogenate showed an inhibitory activity against *Pl* and *M. pl.* as well. Furthermore, a good inhibitory activity could be demonstrated for 1-O-stearoyl-sn-glycero-3-phosphocholine and the phospholipid analogues hexadecylphosphocholine (miltefosine) and 1,1-dimethylpiperidinium-4-yl octadecyl phosphate (perifosine).

The finding that a lysophosphatidylcholine (LPC)-compound occurring in the honeybee midgut is responsible for the inhibitory activity against *Pl* and *M. pl.* was unexpected. Generally, lysophosphatidylcholines are well-examined multifunctional molecules that trigger various cellular and genetic mechanisms under physiological and pathological conditions. It must be emphasized that the homeostasis of LPC in tissue is of crucial importance. However, to date, little is known about phospholipid metabolism in insect midguts. Turunen and Kastari [Turunen & Kastari. 1979. Comp Biochem Physiol 62A:933-937] report on the metabolic fate of phosphatidylcholine in the gut of larvae of *Pieris brassicae*. Using radioactive labelled lecithin to elucidate the fate of phospholipids in the larvae of *Pieris brassicae*, these authors demonstrated that dietary lecithin is converted to lysolecithin in the intestinal lumen and that subsequently the lysolecithin is absorbed from the midgut lumen and converted to phosphatidylcholine. However, no reports so far are available for honeybees. There is a general lack of knowledge concerning the physiological role of phospholipids and their digestion, absorption or biosynthesic pathways in insects.

These unexpected findings allow for a new treatment option or prophylaxis of honeybee brood diseases without the use of antibiotics.

Preferably, the compound is used in the treatment or prophylaxis of bee brood diseases caused by gram-positive bacteria. In one embodiment the disease is American foulbrood which is caused by *Paenibacillus larvae* (*Pl*). In another embodiment the disease is European foulbrood caused by *Melissococcus plutonius* (*M. pl*).

A single dose of lysophosphatidylcholine fed to larvae on day one in concentrations up to 1-2% of fresh body weight of bee larvae younger than one day was found to exhibit no higher mortality than found in the control group as assessed on day 7. This concentration by far exceeds the concentration necessary for antimicrobial activity against *Paenibacillus larvae* and *Melissococcus plutonius*, e.g., an MIC value in vitro of 2-5 ppm. Toxicity effects due to LPC accumulation following a treatment in bee products (e.g. honey) cannot be expected. Data on toxic effects of orally ingested LPC due to surfactant activity (e.g. against erythrocytes) in vertebrates are still scarce, however, LPC is contained in many food items. Besides, LPC is a compound that occurs ubiquitously in biological systems, and it is also found at a low concentration in pollen [Andrikopoulos et al. 1985. Phytochemistry 24:2953-2957]. Moreover, lysophospholipids are compounds naturally occurring in bees. Consequently, there is no reason to expect any adverse effects for the honeybees and the larvae. Furthermore, resistance of *Pl* and *M. pl.* against lysophospholipids is unknown so far. All in all, lysophospholipids represent an advantageous and safe option for treatment and prophylaxis of *Pl* and *M. pl.* infections (American foulbrood and European foulbrood, respectively).

The term "lysophospholipid" as used herein refers to naturally occurring lysophospholipids and synthetic lysophospholipids. The lysophospholipid comprises a glycerol backbone to which a polar group (e.g. a phosphocholine group) is bound, a free hydroxy group in position 2 of the glycerol backbone and a saturated or unsaturated fatty acid residue attached to the glycerol backbone. The fatty acid residue of the lysophospholipid has a $C_n$-alkyl chain or a $C_n$-alkenyl chain, wherein n>4. In embodiments, the lysophospholipid comprises an oxidized fatty acid residue.

The term "lysophospholipid analogue" as used herein refers to compounds such as hexadecylphosphocholine (miltefosine) and 1,1-dimethylpiperidinium-4-yl octadecyl phosphate (perifosine) which are structural analogues of alkyl-lysophospholipids. The alkyl residue of the alkyl-lysophospholipid has a $C_n$-alkyl chain or a $C_n$-alkenyl chain, wherein n>4.

According to one preferred embodiment, the lysophospholipid is a lysophosphatidylcholine (LPC).

Preferably, the lysophosphatidylcholine comprises a saturated or an unsaturated $C_5$-$C_{23}$ fatty acid chain, wherein $C_4$-$C_{24}$ means that the number (n) of carbon atoms (chain length) is between 3<n<25. Preferably, the $C_4$-$C_{24}$ fatty acid chain is attached to position 1 of the glycerol backbone and a free hydroxyl group is at position 2 of the glycerol backbone.

Preferably, the lysophosphatidylcholine is selected from the group consisting of 1-O-oleoyl-sn-glycero-3-phosphocholine and 1-O-stearoyl-sn-glycero-3-phosphocholine for which the inventors demonstrated a good in vitro *Pl* inhibitory activity (see examples below).

The natural carbohydrate source of adult honeybees is nectar or honeydew collected in the wild. Inside the hive, the water content of these liquids is reduced to 16-20%, and enzymes (invertase, diastase and glucose oxidase) are added. The final content comprises c. 38% fructose, 31% glucose and other di- or trisaccharides. As protein source, adult bees collect pollen, which is processed by fermentation to bee bread with a protein content of c. 2.5-61%. Depending on the status of the colony, the time of the year and age of a workerbee, a workerbee consumes up to 3.4-4.3 mg pollen/ day. Lipids, vitamins and minerals are essential and are exclusively obtained from pollen. Larvae are fed with high-quality food secreted from hypopharyngeal glands of nurse bees and traces of nectar and pollen. Therefore, a direct transfer of LPC via nurse bees is questionable. For the complete larval development, an amount of c. 25-35.5 mg protein (equaling 125-187.5 mg pollen) is needed. Brood food also contains sugars, about 18% (day 1-3) and up to 45% (day 4-5) [Review: Brodschneider & Crailsheim. 2010 Apidologie 41:278-294].

In one advantageous embodiment, the lysophosphatidylcholine is 1-O-oleoyl-sn-glycero-3-phosphocholine (herein also referred to as oleoyl-LPC) which is the primary lysophospholipid naturally occurring in the midguts of older larvae and adult honeybees. Thus, any adverse effects during treatment are very unlikely. The inventors could demonstrate an in vitro *Pl* and *M. pl.* inhibitory activity of 1-O-oleoyl-sn-glycero-3-phosphocholine of 2.5 µg/mL MIC (MIC=minimum inhibitory concentration). Lysophosphatidylcholines with other fatty acid residues than oleic acid are present in bee midguts as well, but only to an extent of less than 10% of the 1-O-oleoyl-sn-glycero-3-phosphocholine content.

In other advantageous embodiments the compound is a lysophospholipid analogue, preferably an alkyl-lysophospholipid (ALP) such as hexadecylphosphocholine (miltefosine) and 1,1-dimethylpiperidinium-4-yl octadecyl phosphate (perifosine).

In advantageous embodiments the compound is hexadecylphosphocholine (miltefosine) or 1,1-dimethylpiperidinium-4-yl octadecyl phosphate (perifosine). These compounds also showed a good in vitro *Pl* and *M. pl.* inhibitory activity (see below Example 1, Tables 1.1 and 1.2), but are not susceptible to hydrolysis in contrast to, e.g., 1-O-oleoyl-sn-glycero-3-phosphocholine. Miltefosine and perifosine are structural analogues of alkyllysophospholipids. Miltefosine is a drug orally used to treat visceral leishmaniasis [Sindermann et al. 2004. Med Microbiol Immunol 193:173-190].

In preferred embodiments the compound is selected from the group consisting of 1-O-oleoyl-sn-glycero-3-phosphocholine, 1-O-stearoyl-sn-glycero-3-phosphocholine, and a lysophospholipid analogue.

The lysophospholipid analogue preferably is an alkyl-lysophospholipid analogue selected from the group consisting of miltefosine and perifosine.

In embodiments the compound according to the invention is preferably administered to a honeybee colony in an amount effective to kill the vegetative stage of *Paenibacillus larvae* and/or to kill vegetative forms of *Pl* that result from germination of spores. The dosage may be any appropriate therapeutically effective and safe dosage, e.g., an active lysophospholipid-concentration of about 0.01-0.05% in a diet composition for the honeybee colony. The diet composition is preferably fed to worker honeybees.

In other embodiments the compound according to the invention is preferably administered to a honeybee colony in an amount effective to kill *Melissococcus plutonius*. The dosage may be any appropriate therapeutically effective and safe dosage, e.g., an active lysophospholipid-concentration of about 0.01-0.05% in a diet composition for the honeybee colony. The diet composition is preferably fed to worker honeybees.

The term "honeybee colony" as used herein refers to all types of bees present in a bee colony, including e.g. worker honeybees and honeybee larvae. The honeybee colony is an aggregation of honeybees with or without queen and with or without brood. The term honeybee colony also refers to a honeybee swarm. Furthermore, the term honeybee colony also encompasses package bees and artificial swarms.

Another aspect of the present inventions relates to a composition for use in the treatment or prophylaxis of bee brood diseases, wherein the composition comprises a compound as defined above and wherein the composition is administered to a honeybee colony. In specific embodiments the composition may comprise one compound selected from the group consisting of a lysophospholipid and a lysophospholipid analogue. In specific embodiments the composition may comprise a mixture of two or more of these compounds.

In one advantageous embodiment, the composition is a diet composition or a food additive added to a diet composition for honeybees. Accordingly, the compound is an active ingredient in the diet composition fed to the honeybee colony to reduce the overall *Pl* or *M. pl.* load in a colony and to facilitate a transport of the compound in small amounts into larval food. To obtain a diet composition comprising a compound according to the invention, the compound is preferably added in a concentration of about 0.01-0.1%, more preferably about 0.01-0.05%, to any food that could be used to feed bees. Food for honey bees is well known in the art and includes e.g. sucrose solutions, invert sugars, high fructose corn syrups, various fruit syrups, protein patties and other proteinous food without seasonal restriction. In one embodiment, the composition is a diet composition for larvae of honeybees (direct contact treatment). In other embodiments, the composition is a diet composition for nurse bees of honeybees, wherein the composition is fed to honeybee larvae (treatment by feeding, also referred to as trophallaxis).

Preferably, the diet composition comprises the compound according to the invention in a concentration of about 0.01-0.1%, preferably in a concentration of about 0.01-0.05%.

In another aspect the composition is a sprayable composition comprising a compound as described above for treatment or prophylaxis of bee brood diseases, wherein the sprayable composition is administered to a bee colony by spray application with the intention to be ingested by larvae. This sprayable composition is preferably in the form of a solution and may contain emulsifiers, wetting agents, stabilizers, antifoam and antifreeze agents, dispersing agents, water, adjuvant, antisetting agents and enhancers of viscosity. It should preferably lead to a final lysophospholipid or lysophospholipid analogue concentration of about 0.1-100 µg/brood cell. The volume of a worker honeybee brood cell is known to those skilled in the art and, typically, ranges from 250 to 350 µL.

In yet another aspect the composition is a liposome-, microsphere- or nanosphere-based composition comprising a compound as described above for treatment or prophylaxis of bee brood diseases:

For example, the lysophospholipid or lysophospholipid analogue may be an active ingredient in a sprayable liposome composition with e.g. phospholipids to facilitate liposome formation. This sprayable composition can be administered to a bee colony by spray application with the intention to be ingested by larvae. This sprayable lysophospholipid liposome formulation, preferably in the form of a solution, may contain stabilizers, antifoam and antifreeze agents, further dispersing agents, water, adjuvant, antisetting agents and enhancers of viscosity. It should preferably lead to a final concentration of the compound according to the invention of about 0.1-100 µg/brood cell.

In another example, the compound (lysophospholipid or its analogue) may be comprised as an active ingredient in micro- or nanospheres that are contained in a dipping solution for brood combs, wherein the active ingredient is administered to a bee colony by dipping the brood combs into the dipping solution, resulting in a concentration of the compound in the brood cells of the brood combs effective for treatment or prophylaxis of bee brood diseases. This dipping solution comprises additives to generate micro- and nanospheres such as polyethyleneglycol (PEG), emulsifiers, stabilizers and enhancers of viscosity. Dipping brood combs into the dipping solution should preferably lead to a final compound concentration of about 0.1-100 µg/brood cell. The volume of a worker honeybee brood cell is known to those skilled in the art and, typically, ranges from 250 to 350 µL.

In another example, liposome-, micro- or nanosphere-based formulations that contain the active ingredient lysophosphatidylcholine may be used for systemic application in a honeybee colony through the honeybee food or diet. Preferably, the composition may allow to reach a final concentration of about 0.1-1% of the food or diet. This way, the active ingredient will reach the larvae through the trophallactic activity of nurse bees. The addition of emulsifiers and stabilizers is recommended.

Liposomes, micro- or nanospheres suitable for the present invention result from technical procedures that are sufficiently represented in literature (see, e.g., Kumar, *J. Pharm. Pharmaceut. Sci.* 3:234-258, 2000; Malam, *Trends in Pharmacol. Sci.* 30:592-599, 2009; Collnot, *J. Controlled Release* 161:235-246, 2012).

In another aspect, the present invention also relates to a dipping solution for brood combs comprising a compound as defined herein, i.e. a lysophospholipid or its analogue, wherein the compound is administered to a bee colony by dipping the brood combs into the dipping solution, resulting in a concentration of the compound in the brood cells of the brood combs effective for treatment or prophylaxis of bee brood diseases. Accordingly, the lysophospholipid or its analogue is an active ingredient in the dipping solution for brood combs. This dipping solution may further comprise emulsifiers, wetting agents, antifoam agents, stabilizers and enhancers of viscosity.

Dipping brood combs into the dipping solution should preferably lead to a final concentration of the compound according to the invention of about 0.1-100 µg/brood cell. The volume of a worker honeybee brood cell is known to those skilled in the art and, typically, ranges from 250 to 350 µL.

In yet another aspect, the present invention also relates to a beeswax composition for use in the treatment or prophylaxis of bee brood diseases, wherein a compound as defined herein, i.e. a lysophospholipid or its analogue, is added as an active ingredient to the beeswax composition, resulting in a concentration of the compound in the brood cells of the brood combs effective for treatment or prophylaxis of bee brood diseases. This may be achieved by coating or grouting wax foundations or wax combs with LPC, with the aim to directly administer LPC to allow direct contact of larvae with LPC in the wax via skin contact or via diet. The addition of wetting agents, emulsifiers and stabilizers is recommended.

Another aspect of the present invention relates to the use of a compound selected from the group consisting of a lysophospholipid and a lysophospholipid analogue as described herein as a disinfectant to kill pathogens causing bee brood diseases. The pathogen preferably is a gram-positive bacterium which is preferably selected from the group consisting of *Paenibacillus larvae* and *Melissococcus plutonius*. For example, the lysophospholipid or its analogue may be the disinfectant component in micro- or nanospheres that are contained in a dipping solution that can be used for the disinfection to prevent bee brood diseases such as American or European foulbrood in brood cells or beekeeping equipment. This dipping solution comprises additives to generate micro- and nanospheres such as polyethyleneglycol (PEG), emulsifiers, stabilizers and enhancers of viscosity.

EXAMPLE 1: ISOLATION OF 1-O-OLEOYL-SN-GLYCERO-3-PHOSPHOCHOLINE FROM ADULT HONEYBEE MIDGUT

Bees were anaesthetized and midguts were removed manually, rinsed with ringer solution and then lyophilized. Midguts were prepared according to the following method. 10 guts were washed in bee-ringer, touched dry and then 200 µL of water and 350 µL of ethanol (96%) were added. For homogenization, ultrasound was applied for 3 s and the homogenate was left overnight. The next morning, the homogenate was centrifuged for 1 min (3000 rpm) and the pellet was discarded. The supernatant was transferred to a new Eppendorf vial and lyophilized. 10 Midguts yielded approximately 5 mg. The lyophilized midgut preparation was kept dry at 4-6° C. until further utilization.

Protocol for obtaining an enriched fraction ready for preparative HPLC: An amount of 10 lyophilized midguts (see above) was dissolved in methanol-water (1:1). An solid phase extraction (SPE, RP-18 phase) was carried out to obtain a fraction of the midgut-lyophilisate with enriched biological activity.

Phosphatidylcholine as well as lysophosphatidylcholines, lysophosphatidylinositol and fatty acid reference compounds (linoleic, oleic, palmitic and stearic acid) were obtained from Sigma-Aldrich.

To ensure that the antibacterial compound was not collected from secretory glands on the bee surface, adult honeybees were taken and their bodies were rinsed in abs. ethanol. After concentration, this eluate was tested for activity as well as injected onto HPLC. It was found that this ablution neither showed antibiotic activity against *Pl* nor could there be found lysophosphatidylcholine in the LC-MS chromatogram.

Nutritional fatty acids found e.g. in pollen collected by bees [Szeẹsna. 2006. J Apic Sci 50:65-79] have been previously identified as antimicrobial constituents, i.e., short- and long-chain fatty acids, the latter with increasing number of double bonds, show activity against *P. larvae* [Feldlaufer et al. 1993. Apidologie 24:95-99]. However, such fatty acids that come into question could not be identified in the active fraction of the midgut extract. Our experiments also show that 1-O-oleoyl-sn-glycero-3-phosphocholine is present only in traces in royal jelly (LC-MS data show that the 1-O-oleoyl-sn-glycero-3-phosphocholine peak is present in 500 times lower concentration as compared to fresh honeybee midgut tissue), whereas 1-O-stearoyl-sn-glycero-3-phosphocholine was found to occur below quantitation level.

Due to the collection of fractions eluting late (concentration of acetonitril >80%), the possibility that lactic acid, produced by a potentially existing lactic acid bacteria (LAB) flora in the midgut was responsible for the antibacterial effect, could be ruled out.

Lipids in pollen (range between 0.8-18.9%) are composed of fatty acids and exert antimicrobial properties together with their nutritional value. Palmitic, stearic, oleic, linoleic and linolenic were found in all 577 pollen samples investigated by Manning [Manning R. 2006. Dissertation. Murdoch University]. The fact that winterbees, which were kept under a pollen- and lipid-free diet (only sugar solution) did also show activity against Pl in their midgut rules out the possibility that this activity was due to the intake of dietary lipids.

Besides, activity against Pl was also found in fully developed bees obtained from natural colonies right before enclosure from their capped cells and in artificially reared bees.

For the evaluation of certain fatty acids and phospholipids, overnight cultures of vegetative forms of Pl were used (for results see Table 1.1).

M. pl. was cultured in liquid Basal Medium (BM) for 4 days at 35° C. and from here serial dilutions were carried out to estimate CFU/ml by plating onto BM agar plates. 5 days later CFU were count and concentration was estimated to be $3.46*10^6$ CFU/ml. For the antimicrobial assay, an inoculum of 50 µl of the liquid culture is added to 1 mL of BM liquid medium. A set of different substances were tested in different concentrations (2, 5 and 10 ppm) in order to find out their inhibitory effect against M. pl growth. For substances tested, concentration applied and results see table 1.2. Three replicates per substance were included in the experiment. 5 days after the experiment was started OE (optical extinction) was measured at 600 nm.

The results shown in Tables 1.1 and 1.2 indicate that for a fatty acid, the presence of at least one double bond is a prerequisite for activity, whereas this feature only increases an already existing activity of lysophosphocholines. It could be clearly shown that the lyso-derivatives of phosphocholine are more potent, but also that lysophosphatidylinositol did not show significant inhibitory activity pointing to the fact that also the choline head group is of relevance. From the protocol used for purification, the possibility that lactic acid may be the compound responsible for the antimicrobial activity could be ruled out.

TABLE 1.1

Antimicrobial activity of fatty acids and phospholipids against Paenibacillus larvae (MIC in ppm)

| Compound | MIC (ppm) | MIC (µM) |
| --- | --- | --- |
| linoleic acid[a,b] | 0.5 | 1.8 |
| oleic acid[a,b] | 1 | 3.5 |
| palmitic acid[a] | >20 | >78 |
| stearic acid[a] | >20 | >70 |
| 1-O-oleoyl-sn-glycero-3-phosphocholine | 2 | >3.8 |
| 1-O-stearoyl-sn-glycero-3-phosphocholine | 5 | >9.5 |
| lysophosphatidylcholine (soy bean)[c] | 2 | |
| phosphatidylcholine (bovine brain)[c] | >50 | |
| L-α-lysophosphatidylinositol | >50 | >80 |
| miltefosine | 3 | 7.4 |
| perifosine | 2 | 4.3 |

[a]solubilzed using DMSO, final concentration not exceeding 5% DMSO in bacteria broth, experiments run in triplicate
[b]toxic to honeybee larvae
[c]molecular weight not exactly defined because of mixtures with different fatty acid chain

TABLE 1.2

Antimicrobial activity of fatty acids and phospholipids against Melissococcus plutonius (MIC in ppm)

| Compound | MIC (ppm) | MIC (µM) |
| --- | --- | --- |
| linoleic acid[a,b] | 1 | 3.6 |
| oleic acid[a,b] | 1 | 3.5 |
| palmitic acid[a] | >15 | >40 |
| stearic acid[a] | >10 | >35 |
| 1-O-oleoyl-sn-glycero-3-phosphocholine | 2 | >3.8 |
| 1-O-stearoyl-sn-glycero-3-phosphocholine | 3 | >5.7 |
| lysophosphatidylcholine (soy bean)[c] | 3 | |
| phosphatidylcholine (bovine brain)[c] | >50 | |
| L-α-lysophosphatidylinositol | >10 | >15 |
| miltefosine | 2 | 4.9 |
| perifosine | 2 | 4.3 |

[a]solubilzed using DMSO, final concentration not exceeding 5% DMSO in bacteria broth, experiments run in triplicate
[b]toxic to honeybee larvae
[c]molecular weight not exactly defined because of mixtures with different fatty acid chain

EXAMPLE 2: ARTIFICIAL LARVAL REARING

First instar larvae were transferred into plastic queen cups and fed the following diets: On the first day 10 µL of diet containing 6% glucose, 6% fructose, 1% yeast extract and 50% royal jelly were fed. Test substances (1-O-oleoyl-sn-glycero-3-phosphocholine (oleoyl-LPC), stearic acid, lysophosphatidylinositol and linoleic acid) were added to the first diet in amounts of 0.5 to 10 µg/larvae. For infection with spores of Paenibacillus larvae, larvae were grafted into 5 µL of diet containing test substances and subsequently 5 µL of diet with about 50 added Pl spores were given. Larvae were not fed on the second day to assure the consumption of the given diet. On the third day 20 µL of diet containing 7.5% glucose, 7.5% fructose, 1.5% yeast extract and 50% royal jelly were fed. Amounts of 30, 40 and 60 µL of diet composed of 9% glucose, 9% fructose, 2% yeast extract and 50% royal jelly were fed on the 4th, 5th and 6th day (method modified after Aupinel et al. [Aupinel et al. 2005. Bull Insectol 58:107-111]. Larvae were incubated at 34.5° C. and 95% relative humidity which was reduced to 80% on day 7. The mortality was checked daily for the first 7 days and when individuals emerged from queen cups at day 18 after the transfer into cups. To reduce the time for sporulation of Pl in the lab for security reasons, infection tests with Pl spores were stopped at day 7 with some experiments extend to day 12.

Pollen is part of the larval diet under natural conditions. Its lipid content, which is highly variable, plays a role in nutrition and cell membrane function. It has been stated that free fatty acids such as linoleic acid, which is present in certain pollen decrease the susceptibility of the larvae towards American foulbrood [Feldlaufer et al. 1993. Apidologie 24:95-99]. Under artificial rearing conditions, the diet is devoid of pollen, therefore, an influence of dietary lipids from pollen can be ruled out. Our results are in agreement with an observed influence of pollen on the susceptibility of honeybee larvae at the age of 6-18 h to Paenibacillus larvae that could be assigned to the presence of lipids such as lysophospholipids and free fatty acids in the pollen [Rinderer et al. 1974. Journal of Invertebrate Pathology 23:347-350].

FIG. 1 shows the survival rates (Kaplan-Meier curves) of each 48 larvae fed with different substances (see legend: non treated—control; Lino—linoleic acid 12 µg/larva; Ster— stearic acid 10 μg/larva; LPI—lysophosphatidylinositol—5 μg/larva; LPC10—1-O-oleoyl-sn-glycero-3-phosphocholine—10 μg/larva).

In a separate rearing experiment using a penicillin G and streptomycin enriched larval diet under axenic conditions, we have ruled out the possibility that the bacterial midgut flora is responsible for the antimicrobial activity of honeybee midgut. The midguts of such imagines did exert the same antimicrobial activity against Pl than found for naturally raised imagines.

EXAMPLE 3: BACTERIAL ASSAYS AND SPORE PREPARATION 3.1 Antimicrobial Assays (Inhibition Zone Assay and Liquid Medium Assay) Using Vegetative Forms of Paenibacillus larvae (Pl)

As test organisms, several different strains of Paenibacillus larvae were used.

Overnight cultures of the vegetative forms of bacteria were prepared in BHI (brain heart infusion) liquid medium.

From these overnight cultures, an inoculum of 50 μl is added to 1.0 ml of BHI liquid medium to perform the bacterial test in liquid medium. The compound 1-O-oleoyl-sn-glycero-3-phosphocholine (oleoyl-LPC) together with a positive control was then added at concentrations of 2, 5 and 10 ppm and the test tubes were incubated for 24 h at 34.5° C. Then, the extinction of the solution was measured photometrically. The minimum inhibitory concentration (MIC) for 1-O-oleoyl-sn-glycero-3-phosphocholine and miltefosine (Sigma-Aldrich) was found to be between 2 and 5 ppm.

Figure 2:
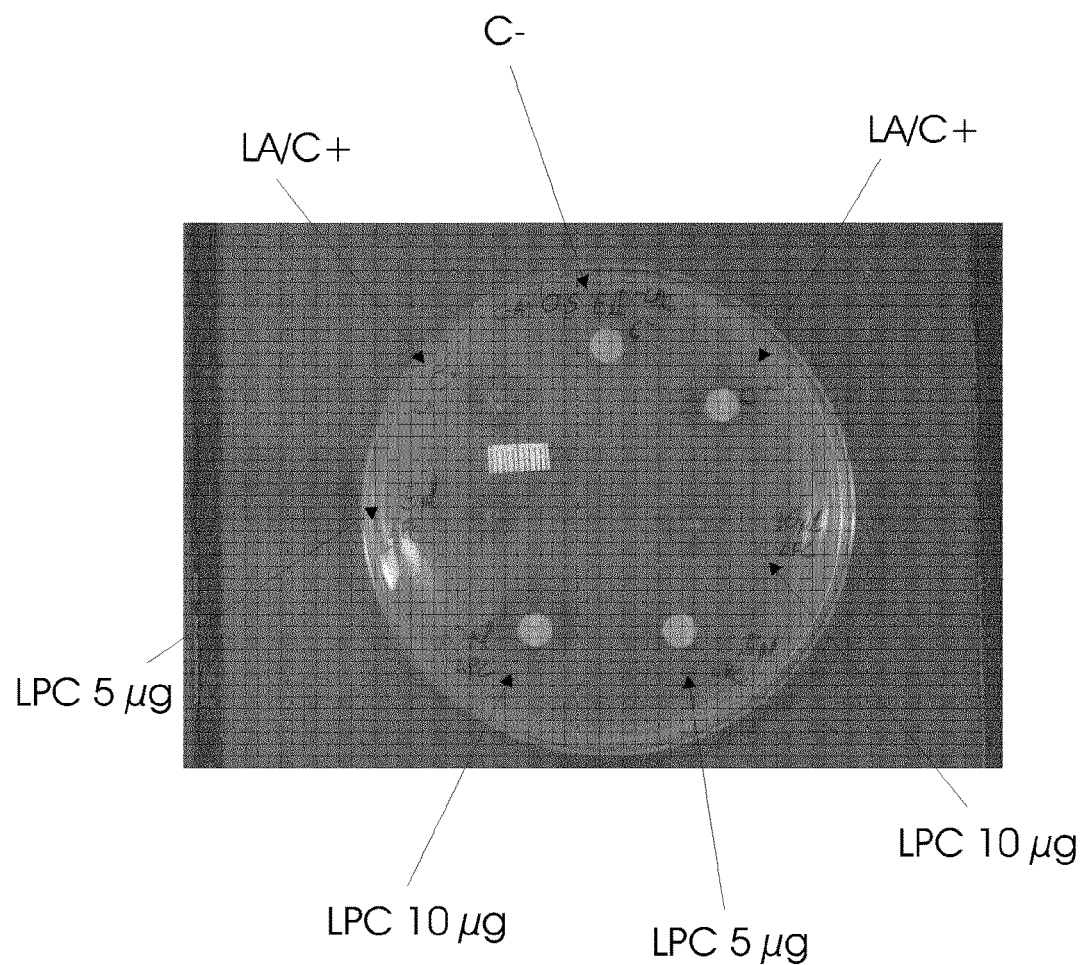
FIG. 2 depicts the results of a zone inhibition test.

For the inhibition zone test, 500 μL of overnight culture were added to 15-20 mL of Columbia agar, mixed and poured onto a petri dish. After the agar solidified, either punched wholes are filled with different amounts of test compounds or test compounds are pipetted on paper discs (5 mm Ø). The plate is then incubated for 24 h (34.5° C.) and zones of inhibition are measured and given in mm. The results are given in FIG. 2 and Table 3.1. Lactic acid and penicillin G were used as positive controls.

LEGEND FIG. 2

CA—Columbia Agar
LPC—1-O-oleoyl-sn-glycero-3-phosphocholine
LA—lactic acid
C+—positive control (lactic acid)
C—water on paper disk
E II—Eric II (test strain of Pl)

TABLE 3.1

| Compound | Amount (μg) | Inhibition zone (mm) |
|---|---|---|
| LPC | 5 | 3.5 |
| LPC | 10 | 5 |
| LA (C+) | 30 | 5 |
| C− | 10,000 | 0 |

3.2 Spore Preparation and Spore Assay

A stock solution containing spores at a known concentration is used to inoculate c. 100 spores/mL medium. This assay is carried out in 20 mL cultivation tubes containing 1.0 mL of BHI (brain heart infusion) liquid medium. To this medium containing c. 50 spores, test compounds are added at different concentrations (e.g., 2, 5 and 10 ppm), together with positive control (penicillin G at 5 ppm) and blank control.

To verify inoculation with c. 100 spores/mL, tubes containing BHI+spores are plated out immediately on agar plates to assess the number of colony forming units (CFU) after 6 days of incubation at 34.5° C.

For the control of viability of the spores, the turbidity (due to germination of spores and formation of vegetative forms) of tubes containing BHI+spores is evaluated on day 4.

For the test probes, bacterial growth is evaluated on day 4 and 6. For those tubes which are negative for bacterial growth, the whole medium (c. 1 mL) is plated onto agar plates and evaluated for CFUs after 2 and 6 days of incubation. CFUs visible after two days result from vegetative forms, while CFUs appearing after 4 days stem from spores.

The results of these tests allow identifying whether the tested compounds have an effect on spore germination in liquid medium and the viability of the spores as assessed by their germination on agar plates.

In order to compare CFU by treatment conditions (control, LPC 5 and 10 ppm, miltefosine 5 and 10 ppm added to vial containing 114.6±28.4 spores for 4 and 6 days), the non-parametric Kruskal-Wallis test was performed. In addition, pairwise comparisons were performed by means of the Mann-Whitney U-test.

Overall, statistically significant differences between the groups were found (Chi$^2$=36.73, p<0.000). Pairwise comparisons yielded significant differences between the controls and all test-groups (Mann-Whitney U tests: p<0.001). Significant differences were found between LPC 5 ppm after 4 days of incubation (before plating the vial content onto agar plates) and LPC 5 ppm after 6 days of incubation (p=0.008). No significant differences were found when comparison for all other groups was performed.

These results indicate that upon germination of spores, all vegetative forms are killed by LPC and miltefosine already at the lowest investigated dose.

EXAMPLE 4: TOXICITY AND TOLERANCE TESTING

Larvae were fed according to a slightly modified rearing method of Aupinel et al., (2005). Larvae were fed for 6 days with different amounts of diets which always contained 50% of an aqueous solution (A, B, C) and 50% royal jelly (w/w). The solutions consisted of yeast extract (A=2%, B=3%, C=4%), glucose and fructose (A=12%, B=15%, C=18% each). 50 g portions of royal jelly (purchased from the Styrian school of beekeepers) were freeze stored at −20° C. Once a day all components of the needed diet were mixed freshly, warmed and fed to the larvae with a micro-pipette. On day 1 and 2 each larva was fed with 10 μL of diet A, on day three with 20 μL of diet B, on day four (30 μL), five (40 μL) and six (50 μL) with diet C. This way, each larva was supported with a total amount of 160 μL of food. The test compounds (see Table 4) were added each at the respective concentration on day 1, i.e. stearic acid (10 μg/larva), lysophosphatidylinositol (5 μg/larva), linoleic acid (12 μg/larva) and oleyol-LPC (10 μg/larva). Each larva was checked for its state of health under the binocular before feeding. A larva was defined healthy when movements of spiracles could be observed and it was shiny and plump. Cups with dead larvae were removed from the plate to prevent infections. To avoid microbial contamination, feeding took place under a laminar flow. Larvae were incubated at 34.5° C. and 90% RH. The mortality rates of the larvae are given below in table 4.1.

TABLE 4.1

Mortality rate of larvae fed with different lipids vs. control

| Treatment | Control (non-treated) | Stearic acid 10 µg/larva | LPI 5 µg/larva | Linoleic acid 12 µg/larva | LPC 10 µg/larva |
|---|---|---|---|---|---|
| $N_{larvae}$ | 525 | 96 | 96 | 48 | 192 |
| $N_{dead\ larvae}$ day 1 | 0 | 0 | 0 | 0 | 0 |
| $N_{dead\ larvae}$ day 2 | 2 | 0 | 0 | 18 | 7 |
| $N_{dead\ larvae}$ day 3 | 2 | 1 | 0 | 2 | 1 |
| $N_{dead\ larvae}$ day 4 | 3 | 0 | 0 | 3 | 1 |
| $N_{dead\ larvae}$ day 5 | 1 | 1 | 1 | 1 | 0 |
| $N_{dead\ larvae}$ day 6 | 2 | 3 | 1 | 1 | 0 |
| $N_{dead\ larvae}$ day 7 | 5 | 1 | 2 | 1 | 4 |
| $N_{dead\ larvae}$ total | 15 | 6 | 4 | 26 | 13 |

In vivo effect of LPC on *Pl*-infected larvae: Artificial larval rearing was performed as described above. Larvae were individually infected with a dose of c. 50 spores/larva (ERIC II, strain 233/00) given on the first day. LPC was administered on day 1, 2 and 3 in a dose of 10 µg/d. Mortality was checked daily until d 12. Results are given in Table 4.2.

TABLE 4.2

Mortality rate of larvae infected with spores of P1 and treated with LPC vs. control in three replicates (spores were given on day 1, LPC doses of each 10 µg/larvae were applied on day 1, 2 and 3

| Treatment | Control (non-treated) | LPC treated 10 µg/larva | LPC+ 50 spores/larva | 50 spores/larva |
|---|---|---|---|---|
| $N_{larvae}$ | 48/48/48 | 70/48/47/48/40 | 71/48/48 | 71/48/48 |
| $N_{dead\ larvae}$ day 1 | 0/0/0 | 0/0/0/0/0 | 0/0/0 | 0/0/0 |
| $N_{dead\ larvae}$ day 2 | 0/0/0 | 0/2/0/0/0 | 1/0/0 | 1/1/1 |
| $N_{dead\ larvae}$ day 3 | 1/0/0 | 0/0/3/0/0 | 3/2/4 | 14/15/11 |
| $N_{dead\ larvae}$ day 4 | 0/0/0 | 1/0/1/0/1 | 11/5/8 | 16/7/10 |
| $N_{dead\ larvae}$ day 5 | 1/1/0 | 0/0/0/0/0 | 7/2/0 | 7/3/0 |
| $N_{dead\ larvae}$ day 6 | 2/0/0 | 1/1/0/0/1 | 1/1/1 | 2/1/1 |
| $N_{dead\ larvae}$ day 7 | 1/0/1 | 0/0/1/0/0 | 1/1/0 | 2/1/1 |
| $N_{dead\ larvae}$ day 8 | 0/0/0 | 2/0/0/0/0 | 0/0/1 | 0/0/0 |
| $N_{dead\ larvae}$ day 9 | 0/1/0 | 1/2/0/3/0 | 0/0/0 | 0/1/1 |
| $N_{dead\ larvae}$ day 10 | 1/0/0 | 2/0/0/0/0 | 2/0/0 | 2/0/0 |
| $N_{dead\ larvae}$ day 11 | 0/1/0 | 0/1/0/0/1 | 0/1/0 | 0/0/0 |
| $N_{dead\ larvae}$ day 12 | 0/0/0 | 2/0/0/0/0 | 0/0/0 | 0/0/0 |
| $N_{dead\ larvae}$ total | 6/3/1 | 9/6/5/3/3 | 26/12/14 | 44/29/25 |
| % Mortality | 12.5/6.3/2.1 | 12.9/12.5/10.6/6.3/7.5 | 36.6/25.0/29.2 | 62.0/60.4/52.1 |

The invention claimed is:

1. A method for the treatment or prophylaxis of one or more bee brood diseases comprising:
    administering to a bee colony a compound selected from a lysophospholipid or an alkyl-lysophospholipid (ALP).

2. The method of claim 1, wherein the one or more bee brood diseases is/are caused by gram-positive bacteria.

3. The method of claim 1, wherein the one or more bee brood diseases comprises American foulbrood.

4. The method of claim 1, wherein the one or more bee brood diseases comprises European foulbrood.

5. The method of claim 1, wherein the compound is a lysophosphatidylcholine.

6. The method of claim 5, wherein the lysophosphatidylcholine comprises a saturated or an unsaturated C4-C24 fatty acid chain.

7. The method of claim 5, wherein the lysophosphatidylcholine is-1-O-oleoyl-sn-glycero-3-phosphocholine or 1-O-stearoyl-sn-glycero-3-phosphocholine.

8. The method of claim 7, wherein the lysophosphatidylcholine is 1-O-oleoyl-sn-glycero-3-phosphocholine.

9. The method of claim 1, wherein the alkyl-lysophospholipid (ALP) is hexadecylphosphocholine (miltefosine) or 1,1-dimethylpiperidinium-4-yl octadecyl phosphate (perifosine).

10. The method of claim 1, wherein the compound is 1-O-oleoyl-sn-glycero-3-phosphocholine, or 1-O-stearoyl-sn-glycero-3-phosphocholine.

11. The method of claim 3, wherein the step of administering comprises administering to a honeybee colony an amount of the compound effective to kill vegetative forms of *Paenibacillus larvae* and/or to kill vegetative forms of *Paenibacillus larvae* that result from the germination of spores.

12. The method of claim 4, wherein the step of administering comprises administering to a honeybee colony an amount of the compound effective to kill *Melissococcus plutonius*.

13. A beeswax composition for use in the treatment or prophylaxis of bee brood diseases comprising:
    beeswax; and
    an active ingredient comprising a compound selected from a lysophospholipid or an alkyl-lysophospholipid (ALP),
    wherein the active ingredient is present in the composition in a concentration effective for treatment or prophylaxis of bee brood diseases.

14. A method comprising:
    using a lysophospholipid or an alkyl-lysophospholipid as disinfectant to kill a pathogen causing a bee brood disease, wherein the pathogen is a gram-positive bacterium selected from the group consisting of *Paenibacillus larvae* and *Melissococcus plutonius*.

15. The method of claim 1, wherein the step of administering comprises dipping brood combs into a dipping solution which comprises the compound.

16. The method of claim 15, which, following the steps of dipping, results in the brood combs having a concentration of the compound in the brood cells of about 0.1-100 µg/brood cell.

* * * * *